United States Patent [19]

Lunn et al.

[11] 4,388,316
[45] Jun. 14, 1983

[54] AMINO-SUBSTITUTED OXAZOLE, OXADIAZOLE AND ISOXAZOLE-SUBSTITUTED CEPHALOSPORINS

[75] Inventors: William H. W. Lunn; William J. Wheeler, both of Indianapolis, Ind.

[73] Assignee: Eli Lilly and Company, Indianapolis, Ind.

[21] Appl. No.: 307,989

[22] Filed: Oct. 2, 1981

[51] Int. Cl.³ .................. A61K 31/545; C07D 501/46
[52] U.S. Cl. .................................... 424/246; 544/22; 544/28; 548/133; 548/246; 548/233
[58] Field of Search .......................... 544/22; 424/246

[56] References Cited

U.S. PATENT DOCUMENTS

| | | | |
|---|---|---|---|
| 3,960,849 | 6/1976 | Breuer | 544/27 |
| 4,024,133 | 5/1977 | Cook et al. | 544/29 |
| 4,200,575 | 4/1980 | Numata et al. | 424/246 |
| 4,258,041 | 3/1981 | O'Callaghan et al. | 424/246 |
| 4,278,671 | 7/1981 | Ochiai et al. | 424/246 |

FOREIGN PATENT DOCUMENTS 2043641 11/1980 United Kingdom .

OTHER PUBLICATIONS

Derwent Abstract 32890.

*Primary Examiner*—Paul M. Coughlan, Jr.
*Attorney, Agent, or Firm*—William B. Scanlon; Arthur R. Whale

[57] ABSTRACT

Broad spectrum cephalosporin antibiotics represented by the formula,

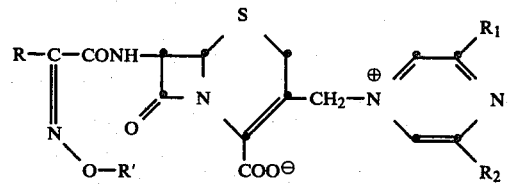

pharmaceutical compositions of the antibiotics, and a method for treating infections are provided. In the formula, R is 2-aminooxazol-4-yl, 5-amino-1,2,4-oxadiazol-3-yl or 5-aminoisoxazol-3-yl; R' is eg. $C_1$–$C_4$ alkyl; $R_1$ is H, $NH_2$, chloro, $C_1$–$C_4$NH—, $(C_1$–$C_4)_2$N—, etc. The antibiotics are best prepared by reacting a pyrazine with a 3-iodomethyl cephalosporin.

14 Claims, No Drawings

AMINO-SUBSTITUTED OXAZOLE, OXADIAZOLE AND ISOXAZOLE-SUBSTITUTED CEPHALOSPORINS

BACKGROUND OF THE INVENTION

This invention is concerned with cephalosporin antibiotics. In particular, it concerns cephalosporin antibiotics substituted in the 3'-position with a pyrazinium or substituted pyrazinium group and in the 7-position with a 2-(amino-substituted oxazole, isoxazole or oxadiazole)-2-oximinoacetylamino group.

A number of semi-synthetic cephalosporin antibiotics substituted in the 3-position with a quaternary ammonium group have been described since cephalosporin $C_A$ (pyridine) was prepared by Hale, Newton, and Abraham, *Biochem. J.* 79, 403 (1961). The well-known clinical antibiotic cephaloridine, 7-(2-thienyl-)acetamido-3-pyridinium-1-ylmethyl-3-cephem-4-carboxylate, U.S. Pat. No. 3,449,338, was the second cephalosporin antibiotic to achieve commercial success following the introduction of sodium cephalothin.

Recently, Heymes, et al., U.S. Pat. No. 4,152,432, describe 7-[2-(2-aminothiazol-4-yl)-2-methoxyiminoacetamido]-3-acetoxymethyl-3-cephem-4-carboxylate as a potent antibiotic. Others have described 3'-quaternary ammonium derivatives of compounds having such an aminothiazole oximino side chain with enhanced potency. For example, O'Callaghan, et al., U.S. Pat. No. 4,258,041, describe the 3-pyridinium-substituted derivative, syn-7-[2-(2-aminothiazol-4-yl)-2-(2-carboxyprop-2-yl)oxyiminoacetamido]-3-(pyridinium-1-ylmethyl)-3-cephem-4-carboxylate. British patent application No. 2,043,641A describes compounds having like 7-position side chains but substituted in the 3'-position with a pyridazinium group.

DETAILED DESCRIPTION

The cephalosporin compounds of this invention are represented by the following structural formula 1

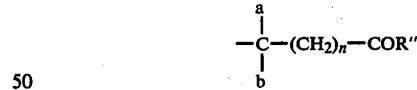

wherein R is an amino-substituted heterocyclic of the formulas

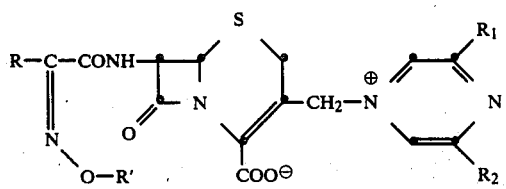

R' is a hydrogen, $C_1$-$C_4$ alkyl, or a carboxy-substituted alkyl or carboxy-substituted cycloalkyl group of the formula

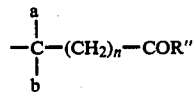

wherein a and b when taken separately are independently hydrogen or $C_1$-$C_3$ alkyl, and when taken together with the carbon atom to which they are attached form a $C_3$-$C_7$ carbocyclic ring; R'' is hydroxy, $C_1$-$C_4$ alkoxy, OR° wherein R° is a carboxy-protecting group, or amino; or R' is a carbamoyl group of the formula

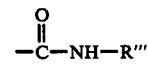

wherein R''' is $C_1$-$C_3$ alkyl, phenyl, or $C_1$-$C_3$ alkyl substituted by phenyl; $R_1$ is hydrogen, $C_1$-$C_4$ alkyl, chloro, amino, $C_1$-$C_4$ alkylamino, di($C_1$-$C_4$ alkyl)amino, $C_2$-$C_4$ hydroxyalkylamino, or di($C_1$-$C_4$ hydroxyalkyl)amino; $R_2$ is hydrogen, or $C_1$-$C_4$ alkyl; and the pharmaceutically acceptable non-toxic salts thereof.

In the above definition of the compounds of the invention, "$C_1$-$C_4$ alkyl" refers to methyl, ethyl, n-propyl, isopropyl, n-butyl, t-butyl, iso-butyl, and sec-butyl; "$C_1$-$C_4$ alkoxy" refers to methoxy, ethoxy, n-propoxy, isopropoxy, sec-butoxy, and the like; "$C_1$-$C_4$ alkylamino" refers to methylamino, ethylamino, n-propylamino, n-butylamino, t-butylamino, and like mono-lower-alkylamines; "di($C_1$-$C_4$ alkyl)amino" refers to dimethylamino, diethylamino, di-n-propylamino, di-n-butylamino, methylethylamino, methyl-n-propylamino, methyl-n-butylamino, and like di-loweralkylamino groups; "$C_2$-$C_4$ hydroxyalkylamino" refers to 2-hydroxyethylamino, 1-hydroxyethylamino, 3-hydroxypropylamino, 4-hydroxybutylamino, 2-hydroxybutylamino, 2-hydroxypropylamino, and the like; and "di($C_2$-$C_4$ hydroxyalkylamino" refers to di(2-hydroxyethyl)amino, di(3-hydroxypropyl)amino, di(4-hydroxybutyl)amino, di(2-hydroxypropyl)amino, and the like.

With respect to the term R' in formula 1, the carboxy-substituted alkyl group (R'' is hydroxy) represented by the formula:

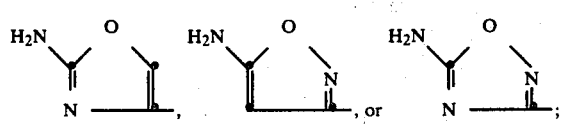

is illustrated by carboxymethyl, 2-carboxyethyl, 1-carboxyethyl, 3-carboxypropyl, 2-carboxypropyl, 4-carboxybutyl, 3-carboxypentyl, 4-carboxyheptyl, 2-carboxybutyl, and the like. When a and b are taken together, examples of the carboxy-substituted $C_3$-$C_7$ carbocyclic rings are 1-carboxycycloprop-1-yl, 1-carboxycyclobut-1-yl, 1-carboxymethylcyclobut-1-yl, 1-carboxycyclopent-1-yl, 1-carboxycyclohex-1-yl, 1-carboxycyclohep-1-yl, 1-carboxyethylcyclopent-1-yl, 1-carboxypropylcyclohex-1-yl, and the like. Examples of such groups when R'' is $C_1$-$C_4$ alkoxy are ethoxycarbonylmethyl, methoxycarbonylpropyl, 2-ethoxycarbonylprop-2-yl, t-butyloxycarbonylmethyl, 3-ethoxycarbonylpropyl, 1-ethoxycarbonylcyclobut-1-yl, 1-(methoxycarbonylmethyl)cyclopent-1-yl, and the groups. Examples of such groups when R'' is amino are aminocarbonylmethyl, 2-aminocarbonylethyl, 3- aminocarbonylpropyl, 2-aminocarbonylprop-2-yl, 1-aminocarbonylcycloprop-1-yl, 1-aminocarbonylcyclohex-1-yl, and like carboxamido-substituted alkyl and cycloalkyl groups.

The compounds of the formula 1 wherein R" is —OR° are carboxy-protected ester derivatives wherein the carboxy group (R" is OH) is protected by a carboxy-protecting ester group, R°, for example, an ester such as t-butyl, 2,2,2-trichloroethyl, 2-iodoethyl, benzyl, substituted benzyl, eg., p-nitrobenzyl, p-methoxybenzyl, and diphenylmethyl; and trialkylsilyl esters such as trimethylsilyl. Such esters are commonly used to temporarily protect the carboxylic acid function in the cephalosporin art during the preparation of antibiotic compounds. These esters of the formula 1 wherein R'" is —OR° are intermediates useful for preparing the free acids wherein R" is hydroxy. The ester function, R°, is removed under known conditions of hydrolysis or hydrogenolysis.

Illustrative of the N-substituted carbamoyl groups, R', are N-methylcarbamoyl, N-ethylcarbamoyl, N-phenylcarbamoyl, N-benzylcarbamoyl, N-(2-phenylethyl)carbamoyl, and the like.

The compounds of the invention represented by the above formula 1 exist in the inner salt form (betaine) characterized by a positively-charged quaternary nitrogen in the 3'-position and the negatively-charged carboxylate anion.

The compounds of the invention can be obtained by alternative preparative methods. According to one method, a 3-halomethyl-substituted cephalosporin represented by the following formula

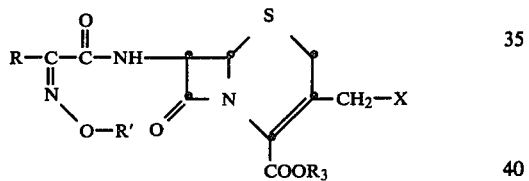

wherein R and R' are as defined hereinabove, X is chloro, bromo or iodo, and R₃ is a carboxy-protecting group; is allowed to react with pyrazine or a substituted pyrazine represented by the formula

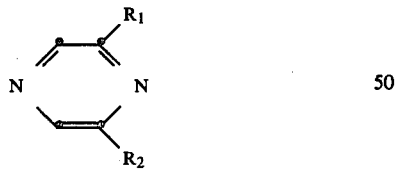

wherein R₁ and R₂ are as defined hereinabove. Preferably, X is iodo and R₃ is a trialkylsilyl ester carboxy-protecting group such as a tri(C₁–C₄ alkyl)silyl ester, for example, trimethylsilyl or triethylsilyl.

The 3-halomethyl-substituted compounds can be prepared by methods known in the art, for example, by the acylation of a 3-halomethyl-7-amino-3-cephem nucleus compound. The preferred 3-iodomethyl compounds of the formula 2 are best obtained by the method described by R. Bonjouklian, U.S. Pat. No. 4,266,049. According to this method, a 7-acylamido-3-acetoxymethyl-3-cephem-4-carboxylic acid is first silylated to block reactive groups such as the C₄ carboxylic acid group and the silylated derivative is reacted with a trialkylsilyliodide, eg., trimethylsilyliodide (TMSI), to form the 3-iodomethyl silylated derivative. The latter is then reacted with pyrazine or the desired substituted pyrazine and the silyl blocks are hydrolyzed to provide a compound of the formula 1. The preparation of compounds of the formula 1 by this method is illustrated by the following general reaction scheme.

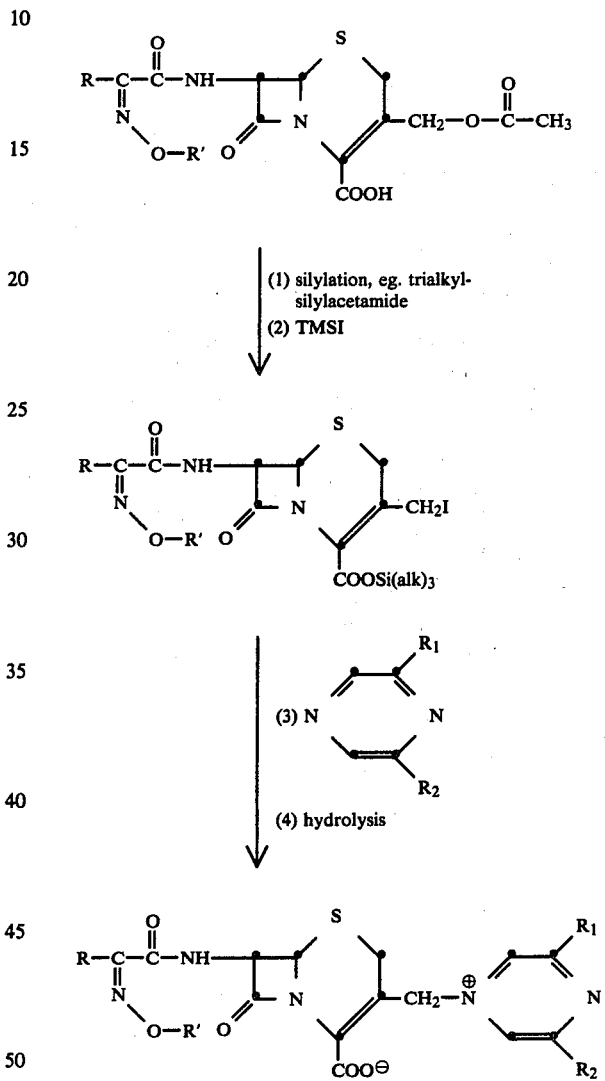

Alternatively, the compounds of the formula 1 can be prepared by the well-known diplacement reaction employing a 3-acetoxymethyl-3-cephem-4-carboxylic acid. The acetoxy group is displaced by the pyrazine to form the pyrazinium compound of the formula 1 as illustrated in the following scheme.

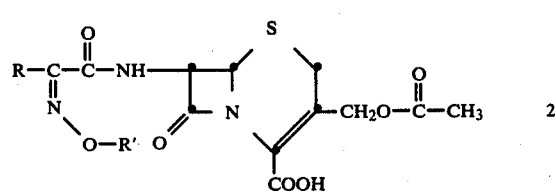

-continued

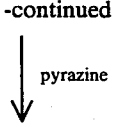

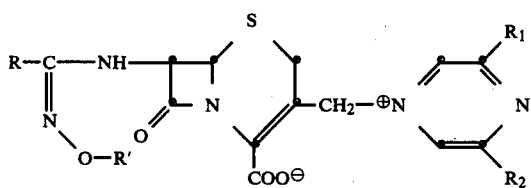

The above reaction is carried out in an aqueous solvent system of water and a water miscible organic solvent such as acetone, DMF, DMAC or other suitable solvent at a temperature between about 20° C. and about 55° C. A small amount of an alkali metal iodide such as sodium iodide may be added to the reaction mixture to enhance the reaction rate and yield of the reaction.

According to another method for preparing the compounds of the invention, a 7-amino-3-(pyrazinium-1-ylmethyl)-3-cephem-4-carboxylate represented by the formula 3:

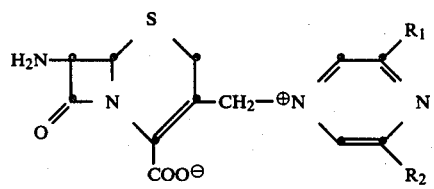

wherein $R_1$ and $R_2$ are as defined by formula 1.

The acylation is carried out by coupling the 2-(aminoheterocyclic)-2-oximinoacetic acid represented by the formula:

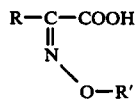

wherein R and R' have the same meanings as defined hereinabove. The N-acylation is carried out by first preparing an active derivative of the carboxy group and then acylating the 7-amino nucleus compound. Active derivatives of the carboxy group which can be used are the active esters formed with hydroxybenzotriazole, N-hydroxysuccinimide, methyl, ethyl, or isobutyl chloroformate, and like active esters.

For purposes of the acylation, when R' is a carboxy-substituted alkyl or cycloalkyl group (formula 1, R" is OH), the carboxy group is protected (formula 1, R"=OR°). The ester group R° is then removed by hydrolysis or hydrogenolysis following the acylation. The oxime hydroxy group (formula 1, R' is hydrogen) need not be protected during the acylation.

The 7-amino-3'-pyrazinium or 3'-substituted pyrazinium compounds of the formula 3 can be obtained by the N-deacylation of a 7-acylamido-3-pyrazinium (or substituted pyrazinium)-1-ylmethyl-3-cephem-4-carboxylate wherein the 7-acyl side chain is other than that in formula 1. For example, cephalosporin G, 7-phenylacetamidocephalosporanic acid, is allowed to react in the displacement reaction with pyrazine or a substituted pyrazine to provide the 3'-pyrazinium-4-carboxylate. The latter is then N-deacylated to remove the phenylacetyl side chain to obtain a 7-amino-3'-pyrazinium nucleus compound represented by the formula 3.

The N-deacylation is carried out in an inert organic solvent, eg., a halogenated hydrocarbon solvent, by allowing the 7-acylamino compound to react with an imido halide-forming reagent such as phosphorus pentachloride. The amide linkage in the 7-position is thus converted to the imido halide which is then converted to an imino ether by the addition of an alcohol, such as methyl alcohol or isobutyl alcohol, to the reaction mixture. The imino ether is hydrolyzed to provide the nucleus compound (formula 3). The nucleus is obtained in the salt form, eg., the hydrochloride salt form, resulting from the acid formed with the imido halide reagent in the reaction.

Examples of 7-amino nucleus compounds represented by the formula 3 are 7-amino-3-pyrazinium-1-ylmethyl-3-cephem-4-carboxylate, 7-amino-3-(3-methylpyrazinium-1-ylmethyl)-3-cephem-4-carboxylate, 7-amino-3-(3,5-dimethylpyrazinium-1-ylmethyl)-3-cephem-4-carboxylate, 7-amino-3-(3-diethylaminopyrazinium-1-ylmethyl)-3-cephem-4-carboxylate, 7-amino-3-[3-di(2-hydroxyethyl)aminopyrazinium-1-ylmethyl]-3-cephem-4-carboxylate, and the salts thereof.

In an example of the preparation of a 7-amino-3-(pyrazinium-1-ylmethyl)-3-cephem-4-carboxylate of this invention, 7-(2-thienylacetamido)cephalosporanic acid is reacted with pyrazine to form the 7-(2-thienylacetamido)-3-(pyrazinium-1-ylmethyl)-3-cephem-4-carboxylate. The latter is then converted to the trimethylsilyl ester on reaction in a halogenated hydrocarbon solvent such as methylene chloride or trichloroethane with trimethylchlorosilane in the presence of an amount of dimethylacetamide corresponding to a 4-5 molar excess. The solution of the silyl ester is cooled to a temperature of about $-30°$ C. to about $0°$ C. and an imino halide-forming agent such as phosphorus pentachloride is added. The reaction mixture is stirred in the cold for from 1 to 3 hours.

The cold reaction mixture is then treated with an alcohol such as a $C_1$-$C_4$ alkanol, benzyl alcohol or, preferably, a glycol such as propylene glycol or 1,3-butanediol. The temperature of the reaction mixture is then raised to about $-5°$ C. to about $5°$ C. The product precipitates, is filtered, washed with methylene chloride and dried.

During the N-deacylation, any reactive substituent groups of the substituted pyrazinium group ($R_1$ and $R_2$) are protected from reaction with the imino halide-forming reagent. For example, an amino group substituent is protected. Since the 7-amino nucleus compound is used in the preparation of compounds of the invention wherein R is an acyl group via the above-described acylation, the protected substituent group is preferably left intact to likewise protect the substituent group during the subsequent N-acylation.

Alternatively, the 7-amino nucleus compounds represented by the formula 3 can be prepared with 7β-formamidocephalosporanic acid (N-formyl 7ACA). According to this method, N-formyl 7ACA is silylated and the silyl derivative is reacted with trimethylsilyl iodide to form the silylated 7-formamido-3-iodomethyl-3-cephem-4-carboxylic acid. The 3-iodomethyl derivative is prepared by the Bonjouklian method described hereinabove. The 3-iodomethyl silylated derivative is then reacted with pyrazine or the substituted pyrazine to form the 7-formamido-3-(pyrazinium-1-ylmethyl)-3-cephem-4-carboxylic acid silylated derivative. The latter is deformylated in methanolic hydrochloric acid to provide the compound of the formula 3 as the hydrochloride salt.

In addition to the bentanine salt form of the compounds of the invention, acid addition salts also can be formed with the compounds of the invention. Such salts are pharmaceutically acceptable non-toxic salts which can be used in formulating suitable antibiotic formulations for administration. Salts can be formed with the mineral acids such as hydrochloric acid, hydrobromic acid, sulfuric acid, and phosphoric acid. Salts formed with strong organic acids such as the aryl and alkyl sulfonic acids, for example, toluenesulfonic acid and methanesulfonic acid, also can be formed with the compounds of the formula 1 by conventional methods. The salts formed with the strong acids such as hydrochloric acid are illustrated by the following partial structural formula:

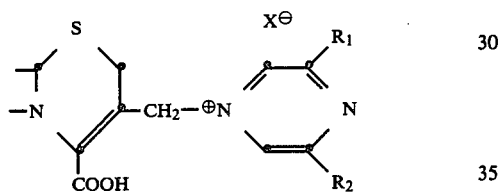

wherein $X^{\ominus}$ is the anion formed with the strong acid. A basic substituent group on the pyrazinium ring such as dialkylamino can also form salts with acids.

The 7-[2-(amino-substituted oxazole and oxadiazole)-2-oximinoacetamido]-3-acetoxymethyl-3-cephem-4-carboxylic acids represented by the formula 2 are prepared by the methods described by Wheeler in copending applications Ser. Nos. 310,140 and 300,159, filed Sept. 8, 1981. As described therein, the 7-[2-(2-aminooxazol-4-yl)-2-methoximinoacetamido]-3-acetoxymethyl-3-cephem-4-carboxylic acid and the corresponding 5-amino-1,2,4-oxadiazol-3-yl compound are prepared by the acylation of an ester of 7-aminocephalosporanic acid with the 2-(2-aminooxazol-4-yl)-2-methoximinoacetic acid and the 2-(5-amino-1,2,4-oxadiazol-3-yl)-2-methoximinoacetic acid, respectively.

The 2-(5-amino-1,2,4-oxadiazol-3-yl)-2-methoximinoacetic acid is prepared by reacting an ethyl 2-oximinocyano acetate represented by the formula:

wherein R' is other than hydrogen, with hydroxylamine to obtain a 2-ethoxycarbonyl-2-oximinoacetoxime amide represented by the formula

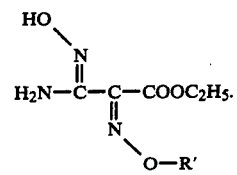

The latter intermediate is reacted with trichloroacetyl chloride to form the cyclization product, an ethyl 2-(5-trichloromethyl-1,2,4-oxadiazol-3-yl)-2-oximinoacetate, represented by the formula

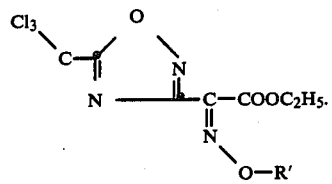

Upon reaction with ammonia, the trichloromethyl substituent is replaced with the amino group to provide the 5-aminooxadiazole derivative represented by the formula

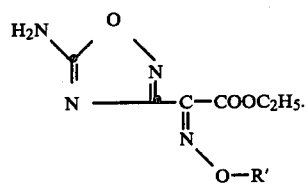

The oximino group of the trichloromethyl-substituted oxadiazole is in both the syn and anti forms. During the aminolysis reaction, the anti (E) compound forms the amide, 2-(5-amino-1,2,4-oxadiazol-3-yl)-2-oximinoacetamide, while the syn (Z) compound does not. Owing to its lower solubility, the antiamide is readily separated from the syn ester. The syn ethyl 2-(5-amino-1,2,4-oxadiazol-3-yl)-2-oximinoacetate is saponified in aqueous ethanolic sodium hydroxide to sodium syn-2-(5-amino-1,2,4-oxadiazol-3-yl)-2-oximinoacetate and the free acid obtained with the salt by treating the salt with hydrochloric acid.

The preparation of the 2-(5-amino-1,2,4-oxadiazol-3-yl)-2-oximinoacetic acid wherein R' is hydrogen is carried out as described above with the oxime protected by a hydroxy-protecting group such as the chloroacetyl group. During the saponification of the ethyl ester, the protecting group is also removed. When R' is a carboxy-substituted alkyl or cycloalkyl group, the 2-oximinocyano acetate represented by the formula,

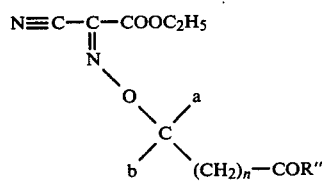

wherein R" is amino or $C_1$–$C_4$ alkoxy is used in the above-described synthesis. When R" is hydroxy, the carboxy group thus represented is protected with a carboxy-protecting group, preferably one that is acid labile such as the p-methoxybenzyl or diphenylmethyl ester group. When R' is an N-substituted carbamoyl group, the heterocyclic free acid wherein R' is hydrogen is acylated with the desired carbamoyl chloride. The carboxy group of the 2-(2-amino-1,2,4-oxadiazol-3-yl)-2-oximinoacetic acid wherein R' is hydrogen is protected with an acid labile ester protecting group, and the oxime group is acylated with the desired carbamoyl chloride, e.g., N-methylcarbamoyl chloride, to provide the desired oximino derivative.

The 2-(2-aminooxazol-4-yl)-2-methoximinoacetic acid is prepared by the zinc oxide catalyzed condensation of urea, a γ-bromo-α-methoxyiminoacetoacetic ester in a suitable organic solvent. Convenient esters are the methyl and ethyl esters. Suitable solvents are the ketones such as acetone, methylethylketone, diethylketone, or methylisobutylketone. The condensation is carried out by suspending zinc oxide in a solution of the urea and the bromoacetoacetic ester in the ketone solvent, and heating the suspension for about 60 hours to about 120 hours. The product is isolated by evaporating the reaction mixture and extracting the product from the concentrate with ethyl acetate. The product is purified by chromatography over alumina.

The 2-(2-aminooxazol-4-yl)-2-methoxyiminoacetic acid is prepared by the saponification of the above ester wherein the 2-amino group is protected. For example, ethyl 2-(2-aminooxazol-4-yl)-2-methoxyiminoacetate is reacted in dimethylacetamide with chloroacetyl chloride in the presence of an acid-binding agent such as tertiary amine, e.g., triethylamine, to form the amino-protected derivative, 2-[2-(2-chloroacetamido)oxazol-4-yl]-2-methoxyiminoacetate. The latter is then deesterified with aqueous sodium hydroxide to sodium 2-(2-aminooxazol-4-yl)-2-methoxyiminoacetate. Upon acidification, the free acid is obtained. During the saponification the amino-protecting chloroacetyl group is likewise removed.

The above-described preparation of the 2-aminooxazole oximino acid is illustrated by the following reaction scheme.

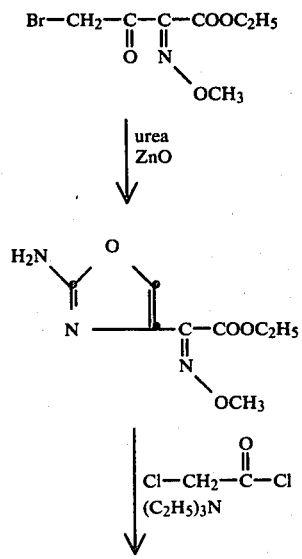

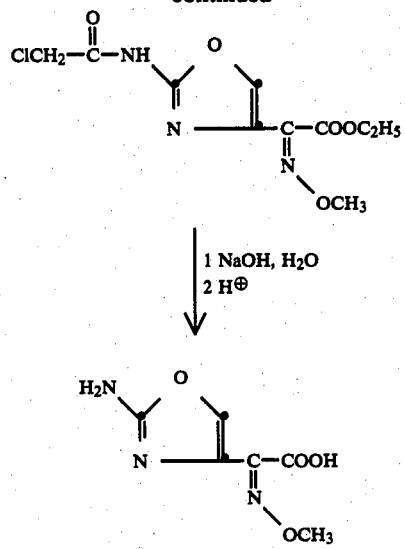

The following are examples of compounds of the invention represented by the formula 1.

| R* | R' | $R_1$ | $R_2$ |
|---|---|---|---|
| AO | $CH_3$ | H | H |
| AO | $CH_3$ | Cl | H |
| AO | $CH_3$ | $CH_3$ | $CH_3$ |
| AO | $CH_3$ | $N(CH_3)_2$ | H |
| AO | $CH_3$ | $N(CH_2H_5)$ | H |
| AO | $-CH_2COOC_2H_5$ | H | H |
| AO | $-C(CH_3)_2COOH$ | H | H |
| AO | H | H | H |
| AOD | $CH_3$ | H | H |
| AOD | $CH_3$ | $CH_3$ | $CH_3$ |
| AOD | $CH_3$ | $N(C_2H_5)_2$ | $CH_3$ |
| AOD | $CH_3$ | $N(C_2H_5)_2$ | H |
| AOD | $-CH_2COOH$ | H | H |
| AOD | $-C(CH_3)_2COOH$ | $NH_2$ | H |
| AOD | $-C(CH_3)_2COOH$ | $N(C_2H_5)_2$ | $C_2H_5$ |
| AOD | H | H | H |
| AIO | $CH_3$ | H | H |
| AIO | H | H | H |
| AIO | $C_2H_5$ | Cl | H |
| AIO | $CH_3$ | $NH_2$ | H |
| AIO | $CH_3$ | $N(C_2H_5)_2$ | H |
| AIO | $-CH_2COOC_2H_5$ | $CH_3$ | $CH_3$ |
| AIO | $-C(CH_3)_2COOH$ | H | H |
| AO | $-(O)NHCH_3$ | H | H |
| AO | $-C(O)NHC_6H_5$ | H | H |
| AOD | $-CH(CH_3)COOH$ | $CH_3$ | H |
| AOD | $-C(O)NHC_2H_5$ | H | $CH_3$ |
| AID | $-C(O)NHCH_2C_6H_5$ | H | H |

*AO is 2-aminooxazol-4-yl; AOD is 5-amino-1,2,4-oxadiazol-3-yl; AID is 5-aminoisoxazol-3-yl.

A preferred group of compounds of the invention are represented by the formula 1 wherein R' is $C_1$-$C_4$ alkyl, especially methyl. Another preferred group is represented when R is 2-aminooxazol-4-yl or 5-amino-1,2,4-oxadiazol-3-yl; R' is methyl; $R_1$ is hydrogen or di($C_1$-$C_4$ alkyl)amino; and $R_2$ is hydrogen.

The cephalosporin compounds of the invention are broad spectrum antibiotics which inhibit the growth of microorganisms pathogenic to man and animals. They are highly active in vitro and in vivo against the gram-negative bacteria such as proteus, pseudomonas, klebsiella, serratia, and enterobacter; and the gram-positive bacteria, staphylococcus and streptococcus.

The antibiotic compounds of the invention and the pharmaceutically acceptable non-toxic salts thereof can be formulated into pharmaceutical compositions suitable for parenteral administration. Accordingly, in a further aspect of this invention there are provided dosage unit formulations of the compounds of the invention comprising between about 100 mg and about 5 g of a compound of the formula 1 with or without an excipient. The dosage unit formulation is suitably made up in ampoules or rubber-stoppered vials containing the antibiotic in solid amorphous or crystalline form. The formulation may also contain a buffering agent, stabilizing agent, wetting agent, solubilizing agent or other excipient.

Such dosage unit forms are employed for administration of the antibiotic via intravenous infusion or intramuscular injection. The dosage unit formulation is dissolved in the desired amount of diluent, eg., Water-for-Injection or 0.9% saline, and administered via syringe (im). Alternatively, the dosage unit formulation can be incorporated in a physiologically acceptable fluid such as 5% Dextrose and administered by the infusion method (iv).

This invention also provides a method for the treatment of bacterial infections in man or animals which comprises administering at a dose between about 100 mg and about 2 g of a compound of the formula 1 or a pharmaceutically acceptable salt thereof. In practicing the therapeutic method, the treatment regimen may vary. For example, the antibiotic may be administered one or more times daily and treatment may continue for several days. The antibiotic is administered im or iv by using known injection and infusion methods. The particular treatment regimen will depend on such factors as the nature and severity of the infection, the age and general health of the patient, as well as the tolerance of the individual toward the antibiotic.

The following Preparations and Examples further illustrate the invention. The abbreviations used in the Preparations and Examples have the following meanings: HPLC is high performance liquid chromatography; E refers to the anti form of the oxime; Z refers to the syn form of the oxime; DMSO/$d_6$ is deuterated dimethylsulfoxide; acetone/$d_6$ is deuterated acetone; n.m.r. is nuclear magnetic resonance spectrum; the letters used to characterize the signals in the n.m.r. spectra refer to the following: s is singlet; d is doublet; q is quartet; m is multiplet; J is the coupling constant in Hertz; br s is broad singlet; and t is triplet.

PREPARATION 1

Preparation of
2-[(5-Amino-1,2,4-oxadiazol)-3-yl]-2-methoxyimino
Acetic Acid

Step A

Preparation of
2-Ethoxycarbonyl-2-methoximinoacetoxime Amide

Ethyl 2-methoxyiminocyanoacetate (8 g, 51.2 mmol) was dissolved in ethanol (2B, 20 ml) and the solution was added dropwise to a mixture of hydroxylamine hydrochloride salt (3.56 g, 51.2 mmol) and sodium carbonate (2.72 g, 25.6 mmol) in 3:2 v:v ethanol/water mixture (25 ml). After the addition was complete, the mixture was stirred and heated at the reflux temperature for approximately sixteen hours. The ethanol was then removed in vacuo and the remaining mixture was further diluted with water and then extracted with ethyl acetate. The ethyl acetate layer was washed with water (3X), dried over magnesium sulfate, filtered and concentrated to an oil in vacuo. The resultant oil later crystallized and was recrystallized from ethanol (2B) to yield 750 mg of the product, 2-ethoxycarbonyl-2-methoximinoacetoxime amide: n.m.r. (DMSO/$d_6$) $\delta$0.82 (t, 3, C$\underline{H}_3$CH$_2$), 3.5 (s, 3, OC$\underline{H}_3$), 3.62 (q, 2, CH$_3$C$\underline{H}_2$—), 5.0 (br s, 2, —N$\underline{H}_2$), 10.15 (s, 1, =NO$\underline{H}$).

Step B

Preparation of Ethyl
2-[(5-Tricholormethyl-1,2,4-oxadiazol)-3-yl]-2-methoxyimino Acetate 2-Ethoxycarbonyl-2-methoximinoacetoxime amide (7.65 g, 40 mmol) and pyridine (5 ml, 45 mmol) were dissolved in dioxane (25 ml) and the solution cooled to 10° C. While stirring this solution, trichloroacetyl chloride (5 ml, 45 mmol) was added dropwise. The mixture was then allowed to warm to room temperature and the stirring was continued for approximately sixteen hours. The mixture was filtered to remove the pyridine hydrochloride and the filtrate was evaporated to dryness.

The residue was triturated with ether and decanted. The ether layer was washed with a saturated aqueous solution of sodium bicarbonate (2X) and then with water (2X), dried over magnesium sulfate, filtered and concentrated. The solid mass remaining was triturated with hexane and decanted. The remaining solid, which was unreacted starting material, was recrystallized from methanol. The hexane solution from the above decantation was evaporated to yield the product compound, ethyl 2-[(5-trichloromethyl-1,2,4-oxadiazol)-3-yl]-2-methoxyimino acetate:(isomeric mixture)mass spectrum:M+315.

Step C

Preparation of Ethyl
2-[(5-amino-1,2,4-oxadiazol)-3-yl]-2-Z-methoximinoacetate

Ethyl 2-[(5-trichloromethyl-1,2,4-oxadiazol)-3-yl]-2-methoximinoacetate (7.62 g) was dissolved in ether (40 ml) and the solution added dropwise to anhydrous ammonia (250 ml) with stirring. Stirring was continued while the ammonia evaporated overnight. The residue was triturated thoroughly with ether. Filtration yielded 1.1 g of the undesired 2-[(5-amino-1,2,4-oxadiazol)-3-yl]-2-E-methoximinoacetamide. The filtrate from above was concentrated in vacuo then recrystallized from 2B ethanol to give 2.2 g of the crude title product.

The crude product was combined with ethyl 2-[(5-amino-1,2,4-oxadiazol)-3-yl]-2-methoximinoacetate (0.83 g) made in a previous experiment analogous to the instant procedure. This mixture was dissolved partially in methylene chloride and filtered. The filtrate was chilled to −40° overnight then filtered again. The filtrate was evaporated to dryness and the residue was crystallized from 2B ethanol, yielding 0.209 g of crystals of the title product. The mother liquor of this crystallization was concentrated and the residue was also recrystallized from 2B ethanol, yielding 0.270 g of the title product. Combination of the yields of these two recrystallizations gave 0.479 g of the desired pure product, ethyl 2-[(5-amino-1,2,4-oxadiazol)-3-yl]-2-Z-methoximinoacetate: n.m.r. (CDCl$_3$) $\delta$1.15 (t, 3, CH$_3$—CH$_2$—O—), 3.95 (s, 3, C$\underline{H}_3$O—N), 4.25 (q, 2, CH$_3$—C$\underline{H}_2$—O), 8.05 (br s, 2, NH$_2$); i.r. (mull) in cm$^{-1}$, 3420 (NH), 1730 (CO$_2$Et), 1670; u.v. (methyl alcohol) λ=227 nm, ε=11,335.

Step D

Preparation of Sodium 2-[(5-amino-1,2,4-oxadiazol)-3-yl]-2-Z-methoximinoacetate Ethyl 2-[(5-amino-1,2,4-oxadiazol)-3-yl]-2-Z-methoximinoacetate (4.28 g, 20 mmol) was dissolved in 2B ethanol (50 ml), followed by addition of 5 N sodium hydroxide solution (4 ml). This reaction mixture was stirred for 0.75 hour at room temperature, then filtered. The solid collected was washed with 2B ethanol and ether to yield 3.43 g (82% yield) of creamcolored crystals of sodium 2-[(5-amino-1,2,4-oxadiazol)-3-yl]-2-Z-methoximinoacetate: i.r. (KBr) 1680, 1665, 1615; u.v. (methanol) λ$_{max}$=233, ε=10,391;

Analysis: Calculated for C$_5$H$_5$N$_4$O$_4$Na: C, 28.86; H, 2.42; N, 26.92; Found: C, 27.37; H, 2.91; N, 23.91.

Step E

Preparation of 2-[(5-Amino-1,2,4-oxadiazol)-3-yl]-2-Z-methoximinoacetic Acid Sodium 2-[(5-amino-1,2,4-oxadiazol)-3-yl]-2-Z-methoximinoacetate (1.0 g) was suspended in ethyl acetate and 1 N hydrochloric acid was added dropwise (6 ml). The layers were separated and the aqueous layer was rewashed with ethyl acetate. The ethyl acetate layers were combined, dried over magnesium sulfate, filtered and the filtrate was evaporated to yield 0.75 g of 2-[(5-amino-1,2,4-oxadiazol)-3-yl]-2-Z-methoximinoacetic acid NMR (CDCl$_3$): δ4.0 (s, 3, N-OCH$_3$), 7.05 (s, 2, NH$_2$), 8.5 (s, 1, CO$_2$H), (DMSO/d$_6$) δ3.75 (s, 3, CH$_3$ON), 8.12 (s, 2, NH$_2$).

PREPARATION 2

Preparation of Benzhydryl 7β-[2-[(5-amino-1,2,4-oxadiazol)-3-yl]-2-Z-methoximinoacetamido]-3-acetoxymethyl-3-cephem-4carboxylate 2-[(5-Amino-1,2,4-oxadiazol)-3-yl]-2-Z-methoximinoacetic acid (0.75 g, 4 mmol) was dissolved in a 1:1 v:v tetrahydrofuran/acetonitrile solvent (20 ml). This solution was stirred as dicyclohexylcarbodiimide (0.5 g, 2.4 mmol), dissolved in the same THF/acetonitrile solvent as above (10 ml), and was added dropwise. The resultant mixture was stirred for 0.5 hour, during which time the dicyclohexylurea precipitated. Benzhydryl 7β-amino-3-acetoxymethyl-3-cephem-4-carboxylate (0.876 g, 2.0 mmoL) was added to the solution and stirring was continued for 56 hours. The dicyclohexylurea was collected by filtration and the filtrate was evaporated, triturated with ether and decanted (2×). The ether-insoluble material was dissolved in ethyl acetate, washed with 1 N hydrochloric acid (2×), aqueous sodium bicarbonate solution (2×), and saturated sodium chloride solution (2×). This solution was then dried over magnesium sulfate, filtered and concentrated in vacuo. The resultant material was again triturated with ether and filtered, yielding 0.640 g of crude material. This material was purified by dry silica gel column chromatography, collecting 25 ml fractions. A 1:1 v:v ethyl acetate/cyclohexane was used as the eluant for the first 25 fractions, followed by elution with a 3:1 v:v ethyl acetate/cyclohexane solvent. Fractions 33 through 42 were combined, evaporated to dryness, dissolved in chloroform and precipitated from the chloroform by the addition of hexane. The precipitate was collected by filtration, washed with ether then dried in vacuo, yielding 0.420 g of benzhydryl 7β-[2-[(5-amino-1,2,4-oxadiazol)-3-yl]-2-Z-methoximinoacetamido]-3-acetoxymethyl-3-cephem-4-carboxylate: n.m.r. (CDCl$_3$) δ1.90 (s, 3, 3'-OAc), 3.27, 3.55 (ABq, J=6, 2, C$_2$-methylene proton), 4.68, 4.95 (ABq, J=5, 2, C$_3$-methine proton), 4.96 (d, J=1.5, 1, C-6 proton), 5.95 (dd, (J=1.5, 3), 1, C-7 proton), 6.25, (br s, 2, NH$_2$), 6.85 (s, 1, CHPh$_2$), 7.20 (s, 10, aromatic protons), 8.72 (d, J=3, 1, 7-amido proton).

PREPARATION 3

Preparation of 7β-[2-(5-Amino-1,2,4-oxa-diazol)-3-yl-2-Z-methoximinoacetamido]-3-acetoxymethyl-3-cephem-4-carboxylic Acid Benzhydryl 7β-[2-(5-amino-1,2,4-oxadiazol)-3-yl-2-Z-methoximinoacetamido]-3-acetoxymethyl-3-cephem-4-carboxylate (0.435 g) was dissolved in a formic acid solution (12 ml, 97–100%) containing triethylsilane (0.3 ml) and stirred for 3 hours. The solution was evaporated to dryness, the residue dissolved in ethyl acetate and extracted with 10% aqueous sodium bicarbonate. The sodium bicarbonate solution was washed with ethyl acetate, then layered with ethyl acetate and the resultant solution was acidified to pH 2 with 1 N hydrochloric acid. The ethyl acetate layer was separated and was washed with saturated sodium chloride solution, dried over magnesium sulfate and filtered. The filtrate was concentrated in vacuo and the residue triturated with ether and filtered to yield 0.215 g of the product compound 7β-[2-[(5-amino-1,2,4-oxadiazol)-3-yl-2-Z-methoximinoacetamido]-3-acetoxymethyl-3-cephem-4-carboxylic acid: n.m.r. (acetone/d$_6$) δ1.7 (s, 3, 3'-OAc), 3.15, 3.42 (ABq, (J=6), 2, C-2 methylene protons), 3.67 (s, 3, N-OCH$_3$), 4.57, 4.8 (ABq, (J=5), 2, C-3 methylene proton), 4.87 (d, (J=2), 1, C-6 proton), 5.65 (dd, (J=2, 2.5), 1, C-7 protons), 7.05 (br, s, 2, -NH$_2$), 8.25 (d, J=2.5, 1, 7-amido proton).

PREPARATION 4

2-(2-Aminooxazol-4-yl)-2-Z-methoxyiminoacetic Acid

Ethyl-γ-bromo-α-methoximinoacetoacetate (100 g, 0.397 mmol), and urea (91 g, 1.98 mmol), were dissolved in methylethylketone (3 l) and zinc oxide (16 g, 0.198 mmol) was added. The suspension was stirred under reflux for 48 hours and was then allowed to cool. The solution was filtered and concentrated in vacuo. The dark residue was dissolved in ethyl acetate and the solution filtered. The filtrate was evaporated in vacuo and the residue was chromatographed over Activity III neutral alumina. The column was eluted sequentially with neat cyclohexane (1000 ml), 1:9 v:v ethyl acetate:cyclohexane (1000 ml), 2.8 v:v ethyl acetate:cyclohexane (2000 ml), 3:7 v:v ethyl acetate:cyclohexane (500 ml), and finally with 1:1 v:v ethyl acetate:cyclohexane until no more product was eluted. Fifty-five fractions were taken, although fractions 51 through 55 were 500 ml or greater. The crude product was contained in fractions 51, 52, and 53. The three fractions were evaporated to give a semi-crystalline mass, each of which were triturated with ether and filtered to yield 3 pure crops of crystals of product. These crops of crystals were combined with a second crop of crystals obtained from fraction 52 to yield 8.9 g of ethyl 2-[2-aminooxazol-4-yl]-2-Z-methoximinoacetate.

A mixture of ethyl 2-[2-aminooxazol-4-yl]-2-Z-methoximinoacetate (2.13 g, 10 mmol), triethylamine (1.53 ml, 11 mmol) and dimethylacetamide (25 ml) were chilled to 0° C. by means of an ice bath. A chilled solution of chloroacetyl chloride (0.939 ml, 11 mmol) in 10 ml of dimethylacetamide was added dropwise to the stirred solution. The reaction mixture was stirred for 0.5 hour at 0° C., and for 19 hours at room temperature. The reaction mixture was poured onto ice and the resultant mixture was extracted with ethyl acetate. The ethyl acetate was washed with water, dried over anhydrous magnesium sulfate, filtered and concentrated in vacuo. After evacuating under high vacuum for 24 hours, the residue was triturated with ether and filtered. The mother liquor was evaporated and the residue was recrystallized from carbon tetrachloride to give 0.456 g of ethyl 2-[2-chloroacetamido)oxazol-4-yl]-2-Z-methoximinoacetate; melting point 91°–92° C.; n.m.r. (CDCl$_3$) δ1.32 (t, 3, —C$\underline{H}_3$, J=7.5 Hz), 4.0 (s, 3, OC$\underline{H}_3$), 4.1 (s, 2, Cl—C$\underline{H}_2$—), 4.37 (q, 2, —O—C$\underline{H}_2$—, J=7.5 Hz), 7.25 (s, 1, aromatic proton).

Sodium hydroxide (5 N, 2 equivalents plus a 10% excess, 4.6 ml, 22.86 mmol) was added dropwise to a stirred suspension of ethyl 2-[2-(chloroacetamido)oxazol-4-yl]-2-Z-methoximinoacetate (3.0 g, 10.38 mmol) in water (90 ml). Dissolution of the ester was complete within about 15 to 20 minutes, and stirring was continued for an additional hour. The mixture was chilled and acidified by the dropwise addition of 1 N hyrochloric acid (6 ml). The aqueous layer was saturated with sodium chloride and the mixture was extracted with large quantities of ethyl acetate. The ethyl acetate extracts were dried over anhydrous sodium sulfate, filtered, combined and concentrated in vacuo, yielding 0.453 g of 2-(2-aminooxazol-4-yl)-2-Z-methoximinoacetic acid; melting point 170°–174° C. (decompose); n.m.r. (DMSO/d$_6$) δ3.84 (s, 3, NOCH$_3$), 6.77 (br, s, 2, amino), δ7.48 (s, 1, aromatic proton).

PREPARATION 5

Benzhydryl 7β-[2-(2-Aminooxazol-4-yl)-2-Z-methoximinoacetamido]-3-acetoxymethyl-3-cephem-4-carboxylate 2-(2-Aminooxazol-4-yl)-2-Z-methoximinoacetic acid (0.261 g, 1 mmol) was dissolved in a mixture of dimethylacetamide (3 ml) and methylene chloride (3 ml). Triethylamine (0.139 ml, 1 mmol) was added to this solution and the resultant mixture was added dropwise to a stirred, chilled solution of iso-butyl-chlorocarbonate in 25 ml of methylene chloride. The reaction mixture was stirred for 1 hour, at the end of which time a methylene chloride (5 ml) solution of benzhydryl 7β-amino-3-acetoxymethyl-3-cephem-4-carboxylate was added dropwise. Initially, the reaction mixture was stirred at 0° to 10° C. and was allowed to gradually warm to ambient temperature and stirred overnight.

The reaction mixture was evaporated in vacuo and the residue was taken up in ethyl acetate. The ethyl acetate solution was washed sequentially with 1 N hydrochloric acid, 10% aqueous sodium bicarbonate and a saturated aqueous sodium chloride solution. Removal of the ethyl acetate solvent in vacuo, after drying the solution over sodium sulfate and filtering, resulted in a yellow foam. This crude product mixture was chromatographed over Activity III Silica Gel (100–200 mesh, Woehlm). Elution was begun with 7:3 v:v ethyl acetate:cyclohexane (fractions 1 through 19), then neat ethyl acetate (fractions 20 through 34), and finally 9:1 v:v ethyl acetate:methanol (fractions 34 through 37). The desired product, benzhydryl 7β-[2-(2-aminooxazol-4-yl)-2-Z-methoximinoacetamido]-3-acetoxymethyl-3-cephem-4-carboxylate, was contained in fractions 14 through 30, and these fractions were combined to yield 0.100 g of the desired product: n.m.r. (CDCl$_3$) δ1.98 (s, 3, methyl of 3-acetoxymethyl), 3,3 and 3.56 (ABq, 2, C-2), 4.75 and 5.01 (ABq, 2, C-3'), 5.02 (d, 1, C-6), 5.25 (br, s, 2, amino), 5.95 (q, 1, C-7), 7.91 (s, 1, benzhydryl methine proton), 7.3 (m, 11, phenyl rings and oxazole ring), 8.42 (d, 1, amido proton).

PREPARATION 6

7β-[2-(2-Aminooxazol-4-yl)-2-Z-methoximinoacetamido]-3-acetoxymethyl-3-cephem-4-carboxylic Acid Benzhydryl 7β-[2-(2-aminooxazol-4-yl)-2-Z-methoximinoacetamido]-3-acetoxymethyl-3-cephem-4-carboxylate (approximately 100 mg, 0.16 mmol) was dissolved in a mixture of formic acid (97–100%, 4 ml) and triethylsilane (0.04 ml, 0.25 mmol). The reaction mixture was stirred at room temperature for 3 hours, was diluted with ethyl acetate, and evaporated to a gum. The gum was treated twice with an ethyl acetate/acetonitrile mixture to give a light-brown powder. The powder was further dried by evaporation in vacuo for 1 hour. The brown powder was then dried with ether for 0.5 hour, sonnicated, filtered and air-dried to yield 64 mg (91%) of 7β-[2-(2-aminooxazol-4-yl)-2-Z-methoximinoacetamido]-3-acetoxymethyl-3-cephem-4-carboxylic acid: n.m.r. (DMSO/d$_6$) δ2.0 (s, 3, acetoxymethyl methyl), 3.4 (m, 2, C-2), 3.85 (s, 3, =NOC$\underline{H}_3$), 4.85 (q, 2, J=16, C-3'), 5.15 (d, 1, J=6, C-6), 5.8 (q, 1, J=4, C-7), 6.85 (s, 2, amino), 7.5 (s, 1, oxazole ring), 9.6 (d, 1, J=9, amido).

PREPARATION 7

7β-[2-(2-Aminooxazol-4-yl)-2-Z-methoximinoacetamido]-3-acetoxymethyl-3-cephem-4-carboxylic Acid A mixture of 1-hydroxybenzotriazole monohydrate (1.02 g, 6.68 mmol) and triethylamine (1.138 ml, 8.16 mmol) in dimethylacetamide (8 ml) was chilled in an ice-acetone bath and a solution of methanesulfonyl chloride (0.57 ml, 7.3 mmol) in 2 ml of dimethylacetamide was added dropwise. The solution was stirred at 0° to 10° C. for 1.5 hours. A solution of 2-(2-aminooxazol-4-yl)-2-Z-methoximinoacetic acid (1.235 g, 6.68 mmol) in dimethylacetamide (2.5 ml) containing triethylamine (1.01 ml) was then added dropwise to the cold mixture, and the solution was stirred at 0° to 10° C. for an additional 1.5 hours. Water (21 ml) was then added dropwise and within 10 minutes after the water had been added, the product precipitated, was collected by filtration, washed with cold water, and dried in vacuo to yield 1.277 g (63%) of the product, 1-(N-oxide)benzotriazol-3-yl 2-[2-aminooxazol-4-yl]-2-Z-methoximinoacetamide.

7β-Amino-3-acetoxymethyl-3-cephem-4-carboxylic acid (0.43 g, 1.58 mmol) was suspended in 25 ml of a 1:1, v:v water:acetone solvent cooled in an ice bath and triethylamine (0.2 ml, 1.48 mmol) was added dropwise to the stirred solution. After the solution formed, 1-(N- oxide)benzotriazol-3-yl 2-[2-aminooxazol-4-yl]-2-Z-methoximinoacetamide (0.5 g, 11.66 mmol) was added portionwise. The pH of the solution was maintained at approximately 7.5 by the periodic additions of 45% aqueous potassium phosphate solution. After the addition of the benzotriazole amide was complete, the mixture was slowly allowed to warm to room temperature. After approximately 2 hours, dissolution had occurred and the solution was stirred overnight. The acetone was removed, and the aqueous concentrate was diluted with water, layered with ethyl acetate, and the pH of the solution adjusted to pH 2.5 by the addition of 1 N hydrochloric acid. The ethyl acetate layer was then separated, dried, filtered and evaporated in vacuo. The partially crystalline residue was triturated with ether and filtered to yield 0.3 g of 7β-[2-(2-aminooxazol-4-yl)-2-Z-methoxyiminoacetamido]-3-acetoxymethyl-3-cephem-4-carboxylic acid: n.m.r. (DMSO/d$_6$) δ2.0 (s, 3, OAc), 3.32 and 3.61 (ABq, 2, J=18 Hz, C-2 protons), 4.85 (s, 3, NOC$\underline{H}_3$), 4.7 and 5.0 (ABq, 2, J=12 Hz, C-3'protons), 5.08 (d, 1, J=4.5 Hz, C-6 proton), 5.72 (q, 1, J=4.5 and 9 Hz, C-7 proton), 6.6 (br, s, 2, amino), 7.38 (s, 1, oxazole aromatic proton), 9.5 (d, 1, J=9 Hz, 7-amido N-proton); u.v. (methanol) λmax=217 ($\epsilon_m$=19,254), λmax=265 ($\epsilon_m$=10,200); Analysis: Calculated: C, 43.74; H, 3.90; N, 15.94. Observed: C, 44.01; H, 3.97; N, 15.75.

EXAMPLE 1 syn-7-[2-(2-Aminooxazol-4-yl)-2-methoxyiminoacetamido]-3-(pyrazinium-1-ylmethyl)-3-cephem-4-carboxylate syn-7-[2-(2-Aminooxazol-4-yl)-2-methoxyiminoacetamido]-3-acetoxymethyl-3-cephem-4-carboxylic acid is suspended in chloroform and the suspension is treated with N-methyl-N-trimethylsilyltrifluoroacetamide at room temperature. The solution of the silylated derivative is treated with a 3-4 molar excess of trimethylsilyliodide (TMSI) to form the corresponding trimethylsilylated 3-iodomethyl compound. The reaction mixture is evaporated to dryness and the silylated product dissolved in acetonitrile, and the solution treated with a small amount of tetrahydrofuran to destroy excess TMSI. A solution of pyrazine in acetonitrile is then added with stirring at room temperature to the solution of the silylated 3-iodomethyl derivative. After the reaction mixture is allowed to stir for about 1.5 hours, sufficient water is added to hydrolyze the trimethylsilyl groups. The product precipitates from the reaction mixture or, when the reaction mixture is more dilute, the product precipitates on dilution of the mixture with diethyl ether.

The product is purified by chromatography, preferably C$_{18}$ silica reverse phase HPLC.

EXAMPLE 2 syn-7-[2-(5-Amino-1,2,4-oxadiazol-3-yl)-2-methoxyiminoacetamido]-3-(pyrazinium-1-ylmethyl)-3-cephem-4-carboxylate is obtained, by following the procedures described by Example 1, with syn-7-[2-(5-amino-1,2,4-oxadiazol-3-yl)-2-methoxyiminoacetamido]-3-acetoxymethyl-3-cephem-4-carboxylic acid by conversion to the silylated 3-iodomethyl derivative and reaction of the latter with pyrazine.

EXAMPLE 3 syn-7-[2-(2-Aminooxazol-4-yl)-2-methoxyiminoacetamido]-3-(3,5-dimethylpyrazinium-1-ylmethyl)-3-cephem-4-carboxylate is prepared with the starting material used in Example 1 and 3,5-dimethylpyrazine by following the procedures described by Example 1.

EXAMPLE 4 syn-7-[2-(5-Amino-1,2,4-oxadiazol-3-yl)-2-methoxyiminoacetamido]-3-(3-diethylaminopyrazinium-1-ylmethyl)-3-cephem-4-carboxylate is prepared, by employing the procedures described by Example 1, with the corresponding 3-acetoxymethyl cephalosporin and 3-diethylaminopyrazine.

EXAMPLE 5 syn-7-[2-(2-Aminooxazol-4-yl)-2-(2-carboxyprop-2-yl)oxyiminoacetamido]-3-(pyrazinium-1-ylmethyl)-3-cephem-4-carboxylate is prepared by reacting syn-7-[2-(2-aminooxazol-4-yl)-2-(2-carboxyprop-2-yl)oxyiminoacetamido]-3-iodomethyl-3-cephem-4-carboxylic acid as the trimethylsilylate derivative with pyrazine by following the procedures described by Example 1.

EXAMPLE 6 syn-7-[2-(5-Amino-1,2,4-oxadiazol-3-yl)-2-ethoxycarbonylmethoxyiminoacetamido]-3-pyrazinium-1-ylmethyl-3-cephem-4-carboxylate is prepared with syn-7-[2-(5-amino-1,2,4-oxadiazol-3-yl)-2-ethoxycarbonylmethoxyiminoacetamido]-3-iodomethyl-3-cephem-4-carboxylic acid, as the trimethylsilylated derivative, and pyrazine by following the procedures described by Example 1.

We claim:

1. A compound of the formula

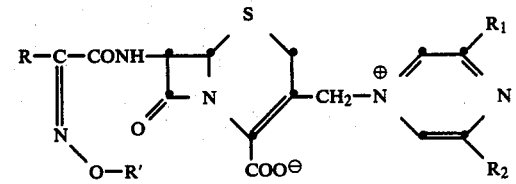

wherein R is an amino-substituted heterocyclic of the formula

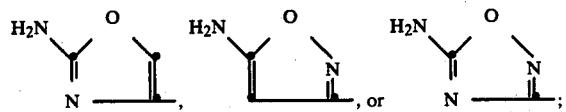

R' is hydrogen, C$_1$–C$_4$ alkyl, or a carboxy-substituted alkyl or carboxy-substituted cycloalkyl group of the formula

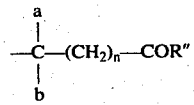

wherein a and b when taken separately are independently hydrogen or C$_1$–C$_3$ alkyl, and when taken together with the carbon atom to which they are attached form a C$_3$–C$_7$ carbocyclic ring; N is 0–3; R″ is hydroxy, $C_1$–$C_4$ alkoxy, amino; or R' is a carbamoyl group of the formula

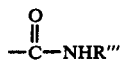

wherein R''' is $C_1$–$C_4$ alkyl, phenyl, or $C_1$–$C_3$ alkyl substituted by phenyl; $R_1$ is hydrogen, $C_1$–$C_4$ alkyl, chloro, amino, $C_1$–$C_4$ alkylamino, di($C_1$–$C_4$ alkyl)amino, $C_2$–$C_4$ hydroxyalkylamino, or di($C_2$–$C_4$ hydroxyalkyl)amino; $R_2$ is hydrogen or $C_1$–$C_4$ alkyl; and the pharmaceutically acceptable non-toxic salts thereof.

2. The compound of claim 1 wherein R' is hydrogen.

3. The compound of claim 1 wherein R' is a group of the formula

4. The compound of claim 3 wherein R'' is hydroxy and a and b are hydrogen or methyl.

5. The compound of claim 1 wherein R' is $C_1$–$C_4$ alkyl.

6. The compound of claim 5 wherein R' is methyl and $R_1$ and $R_2$ are hydrogen.

7. The compound of claim 6 wherein R is 2-aminooxazol-4-yl.

8. The compound of claim 5 wherein $R_1$ is amino, di($C_1$–$C_4$ alkyl)amino, or di($C_2$–$C_4$ hydroxyalkyl)amino, and R' is methyl.

9. The compound of claim 8 wherein R is 2-aminooxazol-4-yl or 5-amino-1,2,4-oxadiazol-3-yl.

10. The compound of claim 9 wherein $R_1$ is diethylamino and $R_2$ is hydrogen.

11. The pharmaceutical composition comprising a therapeutically effective amount of a compound of claim 1 and a pharmaceutically acceptable diluent.

12. The composition of claim 11 in dosage unit form comprising between about 100 mg and about 2 g of the compound of claim 1.

13. The method for treating bacterial infections in a mammal which comprises administering to said mammal an effective dose of between about 100 mg and about 2 g of a compound of the claim 1 or a pharmaceutically acceptable non-toxic salt thereof.

14. The method of claim 13 where in the compound of claim 1 $R_1$ and $R_2$ are both hydrogen.

UNITED STATES PATENT AND TRADEMARK OFFICE
CERTIFICATE OF CORRECTION

PATENT NO. : 4,388,316
DATED : June 14, 1983
INVENTOR(S) : William H. W. Lunn and William J. Wheeler It is certified that error appears in the above—identified patent and that said Letters Patent is hereby corrected as shown below:

Column 18, last line, "N is 0-3" should read -- n is 0-3 --.

Column 19, lines 17-20,

"  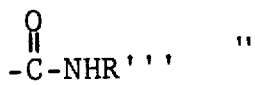  "

should read

-- 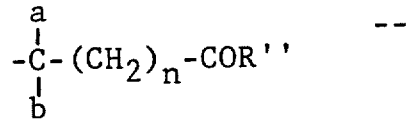 --  .

Signed and Sealed this

Ninth Day of October 1984

[SEAL]

Attest:

Attesting Officer

GERALD J. MOSSINGHOFF

Commissioner of Patents and Trademarks